(12) United States Patent
Mirzatuny

(10) Patent No.: US 11,235,014 B2
(45) Date of Patent: Feb. 1, 2022

(54) HERBAL COMPOSITION FOR THE TREATMENT OF HEADACHE

(71) Applicant: Artashes Mirzatuny, San Francisco, CA (US)

(72) Inventor: Artashes Mirzatuny, San Francisco, CA (US)

( * ) Notice: Subject to any disclaimer, the term of this patent is extended or adjusted under 35 U.S.C. 154(b) by 0 days.

(21) Appl. No.: 16/846,062

(22) Filed: Apr. 10, 2020

(65) Prior Publication Data

US 2020/0323936 A1 Oct. 15, 2020

Related U.S. Application Data

(60) Provisional application No. 62/831,864, filed on Apr. 10, 2019.

(51) Int. Cl.
*A61K 36/00* (2006.01)
*A61K 36/185* (2006.01)
*A61K 31/05* (2006.01)
*A61K 31/352* (2006.01)
*A61K 45/06* (2006.01)

(52) U.S. Cl.
CPC ............ *A61K 36/185* (2013.01); *A61K 31/05* (2013.01); *A61K 31/352* (2013.01); *A61K 45/06* (2013.01); *A61K 2236/333* (2013.01); *A61K 2236/53* (2013.01)

(58) Field of Classification Search
None
See application file for complete search history.

(56) References Cited

U.S. PATENT DOCUMENTS

2011/0085981 A1* 4/2011 Wang .................... A61K 31/70
424/9.2

* cited by examiner

*Primary Examiner* — Michael V Meller
(74) *Attorney, Agent, or Firm* — Foley & Lardner LLP

(57) ABSTRACT

Provided herein are custom therapeutic compositions combining select Chinese herbs and strains of *Cannabis*, methods of making the compositions, and methods of using the composition for treatment of headache pain.

12 Claims, 5 Drawing Sheets

| COMMON TYPES OF CANNABINOIDS ||
|---|---|
| Molecule | Physiological Effect |
| Tetrahydrocannabinol (THC) | Anti-inflammatory, analgesic, antispasmodic, reduces intraocular pressure, reduces skeletal muscle tension |
| Cannabidiol (CBD) | Anti-inflammatory, analgesic, modulates psychoactivity of THC, decreases THC-induced anxiety, sedation and tachycardia |
| Tetrahydrocannabinolic acid (THCA) | Carboxylated form of THC, possibly not as bioavailable as THC |
| Cannabidiolic acid (CBDA) | Carboxylated form of CBD, possibly more bioavailable than CBD |
| Cannabigerol (CBG) | Analgesic, treatment for inflammatory bowel disease, antiseptic, anti-cancer |
| Cannabichromene (CBC) | Anti-inflammatory, analgesic, anti-depressant |

FIG. 1

| TYPES OF TERPENES | | |
|---|---|---|
| Molecule | Natural Sources | Physiological Effect |
| D-limonene | Citrus fruits | Mood elevating, anti depressant |
| Myrcene | Mango, hops | Sedative, muscle relaxer |
| Alpha-pinene | Pine trees | Aids in short-term memory |
| Beta-Caryophyllene | Black pepper, hops | Anti-inflammatory, aids in THC hangover |
| Linalool | Lavender | Analgesic, sedative and anasthetic |

FIG. 2

| CONSTITUENT HERBS OF CUSTOM COMPOSITION ||||| 
|---|---|---|---|---|
| Standard Species | English Common | Pharmaceutical Name | Pinyin | Content (grams) |
| Mentha Haplocalyx | Field mint | Mentha haplocalycis Herba | Bo He | 24 |
| Ligusticum chuangxiong | Szechuan lovage root | Chuangxiong Rhizoma | Chuan Xiong | 12 |
| Angelica dahurica | Dahurian Angelica root | Angelicae dahuricae Radix | Bai Zhi | 6 |
| Notopterygium incisum | Notopterygium root | Notopterygii Rhizoma seu Radix | Qiang Huo | 12 |
| Schizonepeta tenuifolia | Schizonepeta stem or bud | Schizonepeta Herba | Jing Jie | 4.5 |
| Saposhnikovia divaricata | Siler root | Saposhnikoviae Radix | Fang Feng | 6 |
| Glycyrrhiza uralensis | Licorice root | Glycyrrhizae Radix | Gan Cao | 6 |
| Camellia sinensis | Green tea | Folium Camelliae Sinensis | Cha Ye | 2 |
| Lonicera japonica | Honeysuckle flower | Lonicerae Flos | Jin Yin Hua | 9 |
| Juncus effusus | Juncus pith | Junci Medulla | Deng Xin Cao | 3 |
| Corydalis yanhusuo | Corydalis rhizome | Corydalis Rhizoma | Yan Hu Sou | 12 |
| Vitex trifolia | Vitex fruit | Viticis Fructus | Man Jing Zi | 9 |
| Gastrodia elata | Gastrodia rhizome | Gastrodiae Rhizoma | Tian Ma | 6 |
| Scutellaria baicalensis | Baical Skullcap root | Scutellariae Radix | Huang Qin | 8 |
| Lycium barbarum | Lycium fruit | Lycii Fructus | Gou Qi Zi | 15 |
| Paeonia lactiflora | White peony root | Paeoniae Radix alba | Bai Shao | 12 |

FIG. 3

HERBAL COMPOSITION FOR THE TREATMENT OF HEADACHE

CROSS-REFERENCE TO RELATED APPLICATIONS

This application claims the benefit of U.S. Provisional Patent Application No. 62/831,864, filed Apr. 10, 2019, which is incorporated by reference herein in its entirety.

BACKGROUND

The World Health Organization's (WHO) Atlas of Headache Disorders states that roughly 47% of the global population has some form of current headache disorder, meaning they have been symptomatic at least once in the last year (World Health Organization, 2011). Headache is also an expensive illness, with sufferers afflicted not only by pain but also decreased productivity, days lost from work, and hospital visits (Edmeads and Mackell 2002). It is estimated that $14.4 billion dollars are lost each year due to decreased quality of life and disability due to headaches (Lochte 2017).

The most common treatment for tension-type headache are over-the-counter (OTC) analgesic drugs, including aspirin, acetaminophen and ibuprofen. These drugs all function similarly for the episodic treatment of headache by irreversibly binding to cyclooxygenase-1 (COX-1) and cyclooxygenase-2 (COX-2) enzymes. By inhibiting these enzymes' function, inflammation and pain-inducing prostaglandins cannot be synthesized. Lowered prostaglandin levels lead to a decrease in pain and headache (Macdonald 2013). However, the American Association of Family Practitioners (AAFP) recommends that these drugs not be used more than twice weekly, as rebound headache can occur (Millea 2002). A rebound headache results from decreasing analgesic drug concentration in the body. This also may be associated with nausea, poor appetite, irritability and poor concentration (Rapoport, 1996). Furthermore, drugs like acetaminophen and ibuprofen can have major side effects ranging from liver and kidney damage (Plaisance, 2000), to the recently discovered deleterious effects of these drugs on human fetal sex germ cells (Hurtado-Gonzalez, 2018).

Chinese herbal medicine has been shown to be effective for the treatment of tension type headache. However, the amount of peer-reviewed literature is limited in its scope and scientific rigor. For example, in most studies researching the efficacy of Chinese herbal medicine (CHM) for headache, classical pattern diagnosis and differentiation is not a major component of prescription. *Cannabis indica* has similarly been included in many European and North American pharmacopeias for the treatment of migraine headache. However, due to persistent legal constraints, there is a paucity of peer-reviewed studies of *Cannabis* pharmacology as it pertains to headache treatment, and those that exist are limited in scope.

Thus, there remains a need for the identification of reproducible, therapeutically-effective compositions and methods comprising *Cannabis* and Chinese herbs that deliver persistent headache abatement without the unintended side effects of over-the-counter options.

SUMMARY

In one aspect, a composition is provided comprising therapeutically effective amounts of *Cannabis* and the herbs *Corydalis yanhusuo*, *Paeonia lactiflora*, *Ligusticum chuangxiong*, *Angelica dahurica*, and *Scutellaria baicalensis*, wherein the therapeutically effective amounts ameliorate or prevent symptoms associated with headache. In some embodiments, the composition further comprises the herbs *Mentha Haplocalyx*, *Notopterygium incisum*, *Schizonepeta tenuifolia*, *Saposhnikovia divaricate*, *Glycyrrhiza uralensis*, *Camellia sinensis*, *Lonicera japonica*, *Juncus effuses*, *Vitex trifolia*, *Gastrodia elata*, *Lycium barbarum*, and *Paeonia lactiflora*. The mass ratio of *Corydalis yanhusuo:Scutellaria baicalensis:Ligusticum chuangxion:Mentha Haplocalyx: Angelica dahurica:Notopterygium incisum:Schizonepeta tenuifolia:Saposhnikovia divaricate:Glycyrrhiza uralensis: Camellia sinensis:Lonicera japonica:Juncus effuses:Vitex trifolia:Gastrodia elata:Lycium barbarum:Paeonia lactiflora* is about 12:8:12:24:6:12:4.5:6:6:a value between 2 to 6:9:3:9:6:15:12. In an embodiment, the composition comprises an emulsification of (a) an oil extract of the *Cannabis* and (b) an aqueous ethanol extract of the herbs. In some embodiments, the aqueous ethanol extract of the herbs is an extract of an herb blend comprising a ratio of the herbs described herein.

In another aspect a method of forming a composition is provided, the method comprising *Cannabis* and two or more herbs selected from the group consisting of *Corydalis yanhusuo*, *Scutellaria baicalensis*, *Ligusticum chuangxiong Mentha Haplocalyx*, *Angelica dahurica*, *Notopterygium incisum*, *Schizonepeta tenuifolia*, *Saposhnikovia divaricate*, *Glycyrrhiza uralensis*, *Camellia sinensis*, *Lonicera japonica*, *Juncus effuses*, *Vitex trifolia*, *Gastrodia elata*, *Lycium barbarum*, and *Paeonia lactiflora*, and combinations thereof; the method comprising: extracting the *Cannabis* with oil, extracting the two or more herbs with aqueous ethanol, and emulsifying the *Cannabis* extract with the extract of the two or more herbs.

In another aspect, a method of treating or preventing a headache symptom in a subject in need thereof is provided, the method comprising administering to the subject a therapeutically effective amount of a composition comprising an emulsification of (a) an oil extract of *Cannabis* and (b) an aqueous ethanol extract of two or more herbs selected from the group consisting of *Corydalis yanhusuo*, *Scutellaria baicalensis*, *Ligusticum chuangxiong Mentha Haplocalyx*, *Angelica dahurica*, *Notopterygium incisum*, *Schizonepeta tenuifolia*, *Saposhnikovia divaricate*, *Glycyrrhiza uralensis*, *Camellia sinensis*, *Lonicera japonica*, *Juncus effuses*, *Vitex trifolia*, *Gastrodia elata*, *Lycium barbarum*, and *Paeonia lactiflora*, and combinations thereof. In an embodiment, the aqueous ethanol extract is of a blend of all of the herbs in a ratio described herein.

BRIEF DESCRIPTION OF THE DRAWINGS

FIG. 1: A table of the common types of cannabinoids is provided.

FIG. 2: A table of the common types of terpenes found in *Cannabis* is provided.

FIG. 3: A table of constituent herbs included in certain embodiments of the composition is provided.

DETAILED DESCRIPTION

Figure 4:
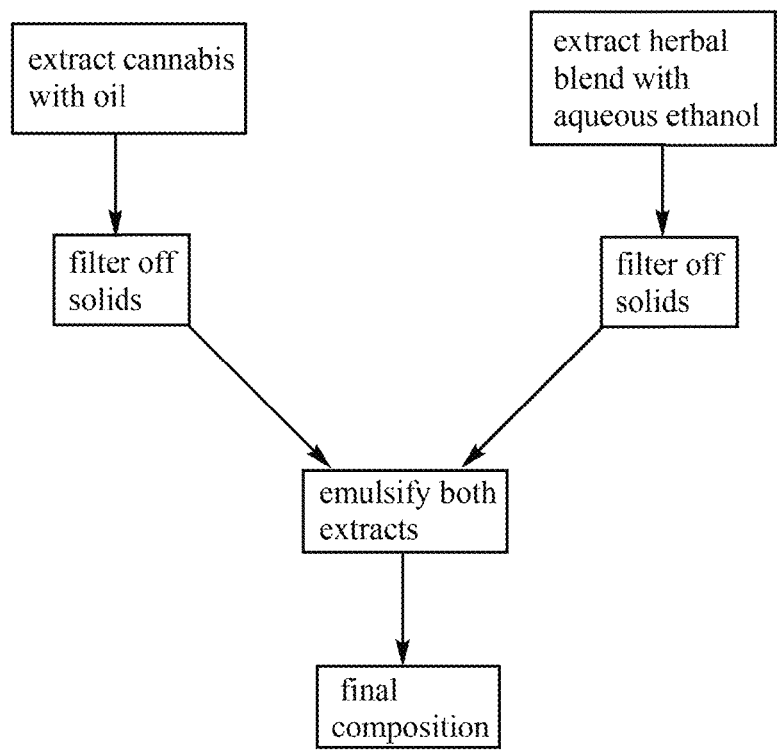
FIG. 4: A schematic illustrating the method of forming the composition described herein, according to some embodiments.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" and "substantially" will be understood by persons of ordinary skill in the art and will vary to some extent depending upon the context in which it is used. If there are uses of the term which are not clear to persons of ordinary skill in the art, given the context in which it is used, "about" and "substantially" will mean up to plus or minus 10% of the particular term.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

As used herein, the terms "subject," "individual," or "patient" can be an individual organism, a vertebrate, a mammal, or a human. "Mammal" includes a human, non-human primate, murine (e.g., mouse, rat, guinea pig, hamster), ovine, bovine, ruminant, lagomorph, porcine, caprine, equine, canine, feline, avis, etc. In any embodiment herein, the mammal is feline or canine. In any embodiment herein, the mammal is human.

The term "administering" a composition to a subject means delivering the composition to the subject. "Administering" includes prophylactic administration of the composition (i.e., before the headache and/or one or more symptoms of the headache are detectable) and/or therapeutic administration of the composition (i.e., after the headache and/or one or more symptoms of the headache are detectable). The methods of the present technology may include administering one or more compounds, compositions or agents. If more than one compound, composition or agent is to be administered it may be administered together at substantially the same time, and/or be administered before, concomitantly with, and/or after administration of another composition or therapeutic procedure (e.g., accupuncture).

As used herein, the terms "effective amount" or "therapeutically effective amount," refer to a quantity sufficient to achieve a desired therapeutic and/or prophylactic effect, e.g., an amount which results in the full or partial amelioration of disorders or symptoms, e.g., those associated with headache in a subject in need thereof. In the context of therapeutic or prophylactic applications, the amount of a composition administered to the subject will depend on the type and severity of the disorder or symptom and on the characteristics of the individual, such as general health, age, sex, body weight and tolerance to drugs or herbs. It will also depend on the degree, severity and type of disorder or symptom. The skilled artisan will be able to determine appropriate dosages depending on these and other factors. The compositions can also be administered in combination with one or more additional compounds, compositions, or herbs. In some embodiments, multiple doses are administered. Additionally or alternatively, in some embodiments, multiple therapeutic compositions or compounds are administered. In the methods described herein, the compositions may be administered to a subject having one or more signs or symptoms of a disorder described herein.

"Treating," "treat," "treated," or "treatment" as used herein covers the treatment of a disease or disorder described herein (e.g., headache), in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, ameliorating, or slowing progression of one or more symptoms of the disease or disorder. Symptoms may be assessed by methods known in the art or described herein, for example, quality of life questionnaires, patient-reported symptom scores, and imaging tests.

"Ameliorate," "ameliorating," and the like, as used herein, refer to inhibiting, relieving, eliminating, or slowing progression of one or more symptoms.

As used herein, "prevention," "prevents," or "preventing" of a disorder, symptom or condition refers to a composition that, in a statistical sample, reduces the occurrence of the disorder, symptom, or condition in the treated subject relative to a control subject, or delays the onset of one or more symptoms of the disorder or condition relative to the control subject.

Throughout this disclosure, various publications, patents and published patent specifications are referenced by an identifying citation. Also within this disclosure are referenced citations, the full bibliographic details of which are provided subsequent to the Examples section. The disclosures of these publications, patents, and published patent specifications are hereby incorporated by reference into the present disclosure to more fully describe the present technology.

1. *Cannabis* Pharmacology:

The *Cannabis* plant is composed of hundreds of biologically active compounds (Backes 2014), including a large class of compounds called cannabinoids. The human body has an innate endocannabinoid system that plant-based phytocannabinoids can bind with and modulate. There are two major cannabinoids receptors in the body: CB1 which is located mostly in central and peripheral neurons and CB2 which is located mostly in immune cells. The major psychoactive compound in *Cannabis* is called delta-9-tetrahydrocannabinol (THC), a CB1 agonist which has a large affinity toward CB1 receptors but can also interact with CB2 as well. It is the acid form of THC, tetrahydrocannabinolic acid (THCA) that is actually produced by the *Cannabis* plant. Through either slow oxidation over time or through exposure to heat, THCA is decarboxylated to the more bioavailable and potent THC (Backes 2014). In addition to being a potent psychoactive substance, THC is also a strong anti-inflammatory and analgesic agent (Russo 2011). Additionally, THC is known to be a strong neuroprotective agent, and reduces intraocular pressure, muscle tension and spasticity (Hampston 1998) (Pacher 2006).

Another cannabinoid found in *Cannabis* is cannabidiol (CBD) which displays allosteric type interaction with CB1 and CB2 receptors, meaning that it does not bind to the primary receptor site. It may be involved in modulating how THC or other cannabinoids bind to CB1 and CB2 receptors (Ivker 2014). Like THC, CBD is the decarboxylated form of cannabidiolic acid (CBDA) which is produced by the *Cannabis* plant. Unlike THCA however, there is research indicating that CBDA is more bioavailable than CBD (Backes 2014). CBD also demonstrates anti-inflammatory and analgesic properties, and may be a potent anticonvulsant.

Cannabigerol (CBG) is the precursor molecule that forms both THC and CBD. There are only a few *Cannabis* varieties that produce a significant amount of CBG up to maturity. CBG is also currently being studied for use in treating inflammatory bowel disease (IBD). CBG is not psychoactive and also has analgesic properties. CBG may also be a useful antiseptic, antibiotic and possible anti-tumor agent (Backes 2014).

Cannabichromene is an uncommon cannabinoid produced by a few *Cannabis* varieties from Central Asia. It is produced more in the immature flower heads than the mature flower. It does not directly bind with cannabinoids receptors (Colasanti 1984). However, it does display anti-inflammatory and analgesic properties as well as possible antidepressant effects in laboratory animals (Deyo 2003).

Referring to FIG. 1, a table of the common types of cannabinoids is provided, summarizing the physiological effect of THC, CBD, THCA, CBDA, CBG, and CBC.

Terpenes are often aromatic compounds, found in *Cannabis* but also many other plants, fruits, and vegetables. The terpenes in *Cannabis* give it the distinctive smells and flavors associated with different strains, as THC and CBD are both odorless and flavorless (Backes 2014). There are over 200 terpenes known to exist in various *Cannabis* strains (Backes 2014). Terpenes are physiologically active and psychologically active.

D-limonene is a terpene found in *Cannabis*, but also found in citrus fruits. It gives some strains of *Cannabis* a stimulating and mood-elevating properties, and has been shown to be helpful with heartburn, anxiety, and as an anti-microbial agent (Ivker 2015).

Myrcene is found in mangoes and hops as well as *Cannabis* and provides the sedative, muscle relaxing effects present in some strains of *Cannabis*. Myrcene has been described as a "potency multiplier", as this terpene can help determine if a particular strain of *Cannabis* is going to be sedating or energizing. If it contains more than 0.5% of myrcene it most likely will be a sedating strain, and if less than 0.5% myrcene it will likely have an energizing effect (Ivker 2015).

Beta-caryophyllene is a terpene found in hops and black pepper. Since it is larger than many other terpene molecules, it typically survives extraction temperatures that smaller terpenes do not, and thus is a very common terpene to be found in *Cannabis* extracts. It is an effective anti-inflammatory when applied either internally and external. It may also prevent certain "foggy headed" side-effects of THC overuse (Russo 2011).

Linalool is found in lavender plants and is mildly psychoactive. It has anti-anxiety and calming effects on the patient. It too has analgesic and anesthetic qualities (Backes 2014).

The interplay between THC, CBD, and terpenes can greatly influence how a particular strain of *Cannabis* affect a patient's mind and body; it is this interplay that provides the typical effects of *Cannabis indica* or *sativa* (Russo 2011). *Indica* strains often have more of the terpenes, like myrcene, that are sedative and calming, while *sativa* strains usually are composed of activating and stimulating terpenes like d-limonene. It also this interplay that may account for clinical effects of whole *Cannabis* extract performing better as anti-convulsants than the synthesized pure THC or CBD counterpart (Russo 2011).

Referring to FIG. 2, a table of the common types of terpenes found in *Cannabis* is provided, along with their natural sources, and physiological effects.

The flowering body of the *Cannabis* plant, in *Cannabis sativa*, *Cannabis ruderalis* and *Cannabis indica* have analgesic properties. It has various names in Chinese Medicine, including mafen ((麻黃)), mabo ((麻勃)), and mahua ((麻花)), all of which refer to the spike-shaped flower of the *Cannabis* plant. It is thought that the term "lightens the body" may refer to *Cannabis*'s analgesic effects (Brand 2017). Additionally, in the *Great Encyclopedia of Chinese Medicinals*, it is stated that mafen "dispels wind, relieves pain, and settles tetany" (Editorial Committee 1977).

2. Compounds of the Disclosure:

A composition combining Chinese herbal formulas along with *Cannabis* extract to deliver a unique composite effect for headache relief is provided herein. This custom herbal composition has been developed utilizing components from traditional Chinese herbal pharmacopeia as well as herbs with more contemporary evidence of analgesia for headaches. The composition also can contain herbs that, per Chinese herbal medicine theory, have a protective component against some of *Cannabis*'s negative effects.

In one exemplary embodiment, the composition can include therapeutically effective amounts of *Cannabis* and the herbs *Corydalis yanhusuo*, *Paeonia lactiflora*, *Ligusticum chuangxiong*, *Angelica dahurica*, and *Scutellaria baicalensis*, wherein the therapeutically effective amounts ameliorate or prevent symptoms associated with headache. In some embodiments, the composition further can include the herbs *Mentha Haplocalyx*, *Notopterygium incisum*, *Schizonepeta tenuifolia*, *Saposhnikovia divaricate*, *Glycyrrhiza uralensis*, *Camellia sinensis*, *Lonicera japonica*, *Juncus effuses*, *Vitex trifolia*, *Gastrodia elata*, and *Lycium barbarum*.

In some embodiments of the composition, the mass ratio of *Corydalis yanhusuo*:*Paeonia lactiflora*:*Ligusticum chuangxion*:*Angelica dahurica*:*Scutellaria baicalensis*:*Mentha Haplocalyx*:*Notopterygium incisum*:*Schizonepeta tenuifolia*:*Saposhnikovia divaricate*:*Glycyrrhiza uralensis*:*Camellia sinensis*:*Lonicera japonica*:*Juncus effuses*:*Vitex trifolia*:*Gastrodia elata*:*Lycium barbarum* can be about 12:12:12:6:8:24:12:4.5:6:6: a value between 2 to 6:9:3:9:6:15. Stated another way, the mass ratio of *Corydalis yanhusuo*:*Paeonia lactiflora*:*Ligusticum chuangxion*:*Angelica dahurica*:*Scutellaria baicalensis*:*Mentha Haplocalyx*:*Notopterygium incisum:Schizonepeta tenuifolia:Saposhnikovia divaricate:Glycyrrhiza uralensis:Camellia sinensis:Lonicera japonica:Juncus effuses:Vitex trifolia:Gastrodia elata: Lycium barbarum can be about 6:6:6:3:4:12:6:2.25:3:3:a value between 1 to 3:4.5:1.5:4.5:3:7.5.

In some embodiments of the composition, the *Cannabis* can be derived from an oil extract. The composition further can include herbs made of an aqueous ethanol extract of *Corydalis yanhusuo*, *Paeonia lactiflora*, *Ligusticum chuangxiong*, *Angelica dahurica*, and *Scutellaria baicalensis*, *Mentha Haplocalyx*, *Notopterygium incisum*, *Schizonepeta tenuifolia*, *Saposhnikovia divaricate*, *Glycyrrhiza uralensis*, *Camellia sinensis*, *Lonicera japonica*, *Juncus effuses*, *Vitex trifolia*, *Gastrodia elata*, and *Lycium barbarum*. In further embodiments, the mass ratio of *Corydalis yanhusuo: Paeonia lactiflora:Ligusticum chuangxion:Angelica dahurica:Scutellaria baicalensis:Mentha Haplocalyx:Notopterygium incisum:Schizonepeta tenuifolia:Saposhnikovia divaricate:Glycyrrhiza uralensis:Camellia sinensis:Lonicera japonica:Juncus effuses:Vitex trifolia:Gastrodia elata: Lycium barbarum*: is about 12:12:12:6:8:24:12:4.5:6:6: a value between 2 to 6:9:3:9:6:15, respectively. Or, stated another way, the mass ratio is about 6:6:6:3:4:12:6:2.25:3:3. The oil and aqueous ethanol extracts can be substantially free of solids. The composition further can include an emulsion of (a) the oil extract of the *Cannabis* and (b) the aqueous ethanol extract of the herbs.

In certain embodiments, the composition comprises from about 1 to about 100 mg of cannabinoids per mg of aqueous ethanol extract. In certain embodiments, the composition includes about 0.01 to 0.1 mg of *Cannabis* derived terpenes per mg of composition. Further embodiments of the composition include a mass ratio of THC:cannabidiol (CBD) between 2:1 to 10:1.

This composition can include many of the constituent herbs of Chuang Xiong Cha Tiao San, with the exclusion of Xi Xin. Xi Xin is known to contain aristolochic acid, which is known to be nephrotoxic (Yang 2014). Chuan Xiong Cha Tiao San is a formula that stops headache on any area of the head due to the inclusion of multiple "wind" herbs. Traditionally, Chuang Xiong (*Ligusticum chuanxiong*) clears wind and alleviates headaches along the temples and vertex of the head (Scheid 2007). Contemporarily, Chuang Xiong has been found to reduce nitric oxide (NO) and cyclooxygenase-2 (COX-2) inflammatory pathways in vitro (Liu 2017). Nitric oxide has been shown in studies to be a pro-nociceptive neurotransmitter, thus reducing formation of nitric oxide may be a potential therapeutic target for analgesic medications (Aley 1998).

Bo He (*Mentha haplocalyx*) benefits the head and eyes (Scheid 2007). Additionally, peppermint a member of the Mentha family has been shown to have positive relaxation effects on the gastrointestinal tract as well as analgesic and anesthetic effects in both the central and peripheral nervous system (Mckay 2006).

Bai Zhi (*Angelica dahurica*) treats frontal headache in Chinese medicine, and has also been shown to suppress NO, COX-2 and interleukin-1B pro-inflammatory pathways (Wang 2015).

Qiang Huo (*Notopterygium incisum*) treats occipital head pain in Chinese Medicine and has contemporarily been identified to inhibit nitric oxide production, which can lead to anti-inflammatory physiological effects (Blunder 2014).

Recent scientific studies have shown that Jing Jie (*Schizonepeta tenuifolia*) suppresses nitric oxide formation and tumor necrosis factor, as well as increases antioxidant activity (Wang 2012).

Fang feng, (*Saposhnikovia divaricate*) is another Chinese herb that can relieve muscle spasms (Benksy 2015). Components of *Saposhnikovia divaricate* have been found to have anti-nociceptive effects in animal models, by down-regulating the expression of COX-2 enzyme (Wu 2016).

Gan cao (*Glycyrrhiza uralensis*) may be used to relieve muscle spasms and alleviate pain (Bensky 2015). The extract of *Glycyrrhiza uralensis* can also diminish the intensity of muscle spasms by inhibiting phosphorylation of Heat Shock Protein 27 (Yang 2017). The antispasmodic effects of Gan Cao can also be helpful in treating muscle tension.

*Camellia sinensis*, also known as green tea or cha ye, is a very common beverage in Asian countries and in traditional Chinese medicine it clears the head. Contemporarily, green tea has been shown to have antinociceptive effects in animal models of pain induction (Arzi 2013). One of the main antioxidants in green tea is epigallocatechingallate (EGCG), which has also been shown to anti-inflammatory and helpful for reducing neuropathic pain (Bimonte 2017).

Jin Yin Hua, *Lonicera japonica*, is traditionally indicated to clear heat and cool the blood and for "clearing-wind heat" (Bensky 2015). This herb may be included in the disclosed composition to help mitigate the warmer nature of *Cannabis*'s TCM temperature. Contemporary research into *Lonicera japonica* extract has determined that it has anti-inflammatory and analgesic qualities, attributed to its ability to inhibit COX-2, nitric oxide synthase and 5-lipoxyfinase (Ryu 2010).

Deng Xin Cao, *Juncus effuses* can be included in presently disclosed compositions to help mitigate the potential for anxiety or tachycardia. Modern research has shown that extract of *Juncus effuses* has anti-inflammatory properties. It has been shown to reduce levels of pro-inflammatory chemical mediators, including nitric oxide, prostaglandin E2 and the cytokines IL-1 B and IL-6 (Park 2016).

Yan hu suo, *Corydalis yanhusuo*, is among the strongest of pain relieving herbs in Traditional Chinese herbology. Traditionally, it is used to invigorate the blood, promote the movement of Qi and alleviate pain (Bensky 2015). When coupled with *Chuan xiong*, the headache relieving qualities of both herbs is synergized. Contemporary research has shown that some of the compounds in Yan Hu Suo induce antinociceptive activity by binding to D2 dopamine receptors (Zhang 2014). Additionally, formula preparations of Yan Hu Suo have been shown to have anti-aging properties as well an anxiolytic effects in laboratory animal models (Li 2017).

Man Jing Zi, *Vitex trifolia*, is traditionally used to clear wind and heat, especially when there is head or eye pain. Additionally, it clears and benefits the head and eyes, particularly along the Liver channel and for red, painful eyes. This herb is included in the presently disclosed compositions not only for the traditional pain relief indications, but also to mitigate against the drying and reddening nature *Cannabis* can have on the eyes. Current research indicates that extracts of Vitex have antinociceptive properties when used in laboratory animal models (Cheng 2010).

Tian ma, *Gastrodia elata*, is used in traditional Chinese Medicine to control and extinguish "Liver Wind." This herb may be particularly useful for treating headaches caused by Liver wind (Bensky 2015). It harmonizes well with *Chuan xiong* for the treatment of wind that leads to migraine and dizziness (Besnky 2015). It may lead to demonstrated reduction in allodynia and hyperalgesia in a rat model for peripheral neuropathy by using *Gastrodia elata* extract (Sun 2012). Additional research has shown that components of *Gastro-*

*dia* extract inhibit pain by decreasing spinal synaptic potentiation, a novel mechanism for pain modulation (Xiao 2017).

Huang Qin, *Scutellaria baicalensis*, is traditionally used as a Heat clearing herb in Traditional Chinese Medicine. Particularly, it sedates ascendant Liver Yang which can manifest as headache, red eyes and irritability (Bensky 2015). Contemporary research has demonstrated that extracts of *Scutellaria baicalensi* have an analgesic effect on acute pain in laboratory animal models (Yimam 2012). *Scutellaria baicalensi* extract may also exhibit analgesic and anti-inflammatory properties when used in a cancer pain study using laboratory animals (Hu 2015).

Gou Qi Zi, *Lycium barbarum*, is a tonifying herb that nourishes the Blood and Yin of the Kidney and Liver in Traditional Chinese Medicine theory. *Cannabis* is described in the Shen Nong Ben Cao Jing as having an acrid and dispersing effect, which is an ideal quality for a pain relieving agent (Bensky 2015). However, these qualities also mean that *Cannabis* can have a drying effect on different parts of the body. This can be seen in the dry, red eyes that sometimes develop after *Cannabis* dosing, as well as dry mouth. The incorporation of Gou Qi Zi into this formula is intended to counteract the drying effects of *Cannabis*. Contemporarily, *Lycium barbarum* has demonstrated anti-oxidant and anti-inflammatory properties (Nardi 2016). Furthermore, *Lycium*'s anti-inflammatory properties may stem from inhibition of the pro-inflammatory NF-KB pathway (Phillippe 2012).

Finally, Bai Shao, *Paeonia lactiflora*, is traditionally also a tonifying herb. It nourishes the Blood as well calms ascendant "Liver Yang." This herb is traditionally used with Gan Cao *Glycyrrhizae radix*, to alleviate muscle spasms and head pain (Bensky 2015). Modern research shows that extracts of *Paeonia lactiflora* have anti-inflammatory and immunomodulatory effects that can suppress pain producing cytokines like prostaglandin E2, leukotriene B4 and nitric oxide (He 2011). Additionally, chemical components of *Paeonia lactiflora* extract have been shown to attenuate neuropathic pain by inhibiting the pro-inflammatory mitogen-activated protein kinase (MAPK) pathway (Zhou 2016).

Referring now to FIG. 3, a list of constituent herbs included in some embodiments of the composition is provided. Included for each herb is the standard species name, English common name, the pharmaceutical name, pinyin, and the content in grams.

3. Methods of Making:

A method of forming a composition including *Cannabis* and two or more herbs selected from the group consisting of *Corydalis yanhusuo, Scutellaria baicalensis, Ligusticum chuangxiong, Mentha Haplocalyx, Angelica dahurica, Notopterygium incisum, Schizonepeta tenuifolia, Saposhnikovia divaricate, Glycyrrhiza uralensis, Camellia sinensis, Lonicera japonica, Juncus effuses, Vitex trifolia, Gastrodia elata, Lycium barbarum*, and *Paeonia lactiflora*, and combinations thereof, is also provided. The method can include: i) extracting the *Cannabis* with oil, ii) extracting the two or more herbs with aqueous ethanol, and iii) emulsifying the *Cannabis* extract with the extract of the two or more herbs.

Referring to FIG. 4, *Cannabis* can be extracted using oil and solids filtered off. Herbal blends may be extracted using aqueous ethanol and solids filtered off. The two extracts may be emulsified to create a final combined composition.

Figure 5:
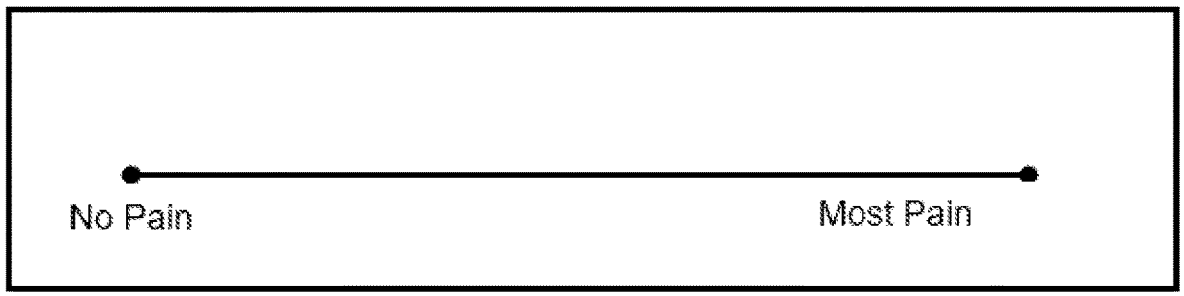
FIG. 5: Visual Analog Scale

Referring to FIG. 5, the pain scale incorporated into these questionnaires was the Visual Analog Scale.

In some embodiments, the two or more herbs can be extracted with aqueous ethanol in a mass ratio of about 12:8:12:24:6:12:4.5:6:6:a value between 2 to 6:9:3:9:6:15 for *Corydalis yanhusuo, Scutellaria baicalensis, Ligusticum chuangxiong, Mentha Haplocalyx, Angelica dahurica, Notopterygium incisum, Schizonepeta tenuifolia, Saposhnikovia divaricate, Glycyrrhiza uralensis, Camellia sinensis, Lonicera japonica, Juncus effuses, Vitex trifolia, Gastrodia elata, Lycium barbarum*, and *Paeonia lactiflora*, respectively.

In some embodiments, the *Cannabis* can be a hybrid of *Cannabis sativa* and *Cannabis indica*. In certain embodiments of the method, the *Cannabis* oil can be extracted by immersing the *Cannabis* in oil for about 6 to about 10 hours, and removing solids to form the extract. In some embodiments, extraction also can occur by immersing the *Cannabis* in oil. About 3.3 to about 4.5 mL of oil may be used per gram of *Cannabis*.

In some embodiments, the herbs can be extracted by immersing them in aqueous ethanol for about 12 hours to about 36 hours, or any range including or up to those two times, and removing solids to form the extract. In some embodiments of the extraction, about 0.5 mL to about 2 mL of aqueous ethanol can be used per gram of the two or more herbs. The aqueous ethanol can be from about 40 to about 60 v/v % ethanol.

In certain embodiments, from about 1 mL to about 100 mL of *Cannabis* extract with about 100 mL to about 200 mL of the herbal extract can be emulsified together. The emulsifying may be achieved through sonication.

4. Methods of Use:

A method of treating or preventing a headache symptom in a subject in need thereof is also provided herein. The method can include administering to a subject a therapeutically effective amount of a composition made of an emulsification of (a) an oil extract of *Cannabis* and (b) an aqueous extract of two or more herbs selected from the group consisting of *Corydalis yanhusuo, Scutellaria baicalensis, Ligusticum chuangxiong, Mentha Haplocalyx, Angelica dahurica, Notopterygium incisum, Schizonepeta tenuifolia, Saposhnikovia divaricate, Glycyrrhiza uralensis, Camellia sinensis, Lonicera japonica, Juncus effuses, Vitex trifolia, Gastrodia elata, Lycium barbarum*, and *Paeonia lactiflora*, and combinations thereof.

In some embodiments, the two or more herbs can be extracted with aqueous ethanol in a mass ratio of about 12:8:12:24:6:12:4.5:6:6:a value between 2 to 6:9:3:9:6:15 for *Corydalis yanhusuo, Scutellaria baicalensis, Ligusticum chuangxiong, Mentha Haplocalyx, Angelica dahurica, Notopterygium incisum, Schizonepeta tenuifolia, Saposhnikovia divaricate, Glycyrrhiza uralensis, Camellia sinensis, Lonicera japonica, Juncus effuses, Vitex trifolia, Gastrodia elata, Lycium barbarum*, and *Paeonia lactiflora*, respectively. The aqueous ethanol extract can be a blend of the herbs.

EXAMPLES

A multi-center clinical trial in an outpatient setting was performed. The study protocol was reviewed for approval by the California Institute for Integrative Studies Human Research Review Committee and Institutional Review Boards Ethics Committees from research facilities. Patients were recruited by participating medical providers at an academic or clinical setting. institutions, as well as by approved ads in news outlets, paper flyers, and on social media, following inclusion and exclusion criteria summarized below. After consenting to participation, participants were asked to complete demographic questionnaires, as well as document headache and health history. A medical doctor conducted an intake exam and interview. Three hundred participants were recruited for this study, with fifty participants in each group.

Inclusion criteria include having a tension type headache as defined by the International Headache Society. Participants were selected if they had headaches lasting from 30 minutes to 7 days, and had those headaches less than 180 days per year or 15 per month, Furthermore, those headaches must have had at least two of the following pain characteristics: pressing or tightening (non-pulsating) quality, mild to moderate intensity (does not completely incapacitate the patient), bilateral location on the head, not exacerbated or aggravated by walking up stairs or any similar routine physical activities.

Exclusion Criteria:

As part of International Headache Society guidelines for tension type headache definitions, prospective study participants were excluded if they had nausea or vomiting accompanying their headaches. Also, prospective participants could only present with photophobia (sensitivity to light) or phonophobia (sensitivity to sound), but not both. Presence of either photophobia or phonophobia was a not a requirement for the study. Other exclusion criteria include: those study applicants having had tension type headaches for less than one year, diagnosed abnormal liver and kidney function, systemic disease, abnormal neurological assessments, applicants currently on prescription triptan-type medications for the treatment for headaches (outside of symptomatic analgesics), hypertension, pregnant women or those seeking to become pregnant, the presence of an organic cause such as a brain tumor, or liver or kidney disease, and persons under the age of 21.

The random control trial included four arms:
1. Control group, consisting of vehicle groups for each separate treatment. (n=150)
   a. Alcohol/water vehicle group (n=50)
   b. Olive oil group (n=50)
   c. Alcohol/water/olive oil (n=50)
2. Custom Chinese herbal formula alone group (n=50),
3. *Cannabis* alone group (n=50), and the
4. Combination Chinese herbal plus *Cannabis* group (n=50).

All groups were randomized by assigning each participant an automatically generated number randomized by software. Each group had the same number of participants. The control group preparation contained only the vehicle for administration. The vehicle is the substrate with which the herbs and *Cannabis* are mixed in. For example, the Chinese herbs were suspended in a mixture of 50% ethanol and 50% water. Ethanol and water, in a 1:1 ratio, is therefore the Chinese herbal groups vehicle. The *Cannabis* group was olive oil, water, and an emulsifying agent; sunflower lecithin. The components of the liquid vehicle, Chinese herbal preparation, *Cannabis* preparation and the combination preparation were all be single lot preparation. All herbal preparations were from the same lot of Chinese herbal formulas and *Cannabis* and were composed from the same lots and manufacturers. These formulations were all tested for contaminants, heavy metals, pesticides and herbicides. A certificate of analysis was kept of file. Participants were allowed to continue symptomatic pharmaceutical analgesics as needed for headache pain, but were asked to record use of these medicines. The study was completed using intent-to-treat.

Treatment lasted for 8 weeks. During treatment, there were 0, 2, 4 and 8-week time points where patients were asked to complete questionnaires regarding: headache frequency, report on intensity of each headache using Visual Analog Pain scale, and report on medication use (i.e. OTC analgesics). The pain scale incorporated into these questionnaires was the Visual Analog Scale (FIG. 5). This pain scale uses a printout of a scale of exactly 100 mm long, with "no pain" and "most pain" at both extremes of the scale. The patient is asked to place a mark on the scale to indicate where their pain is currently. This mark is then measured and quantified. Additionally, the participants were asked how many doses and total volume the patients took for each headache episode. The various time point interviews were used to discuss any side effects or adverse events that any of the study participants experienced. Participants were also able to ask for more of any of the treatments they used in the study. Patients were asked to keep a log regarding their use of both experimental treatment medication and any over-the-counter medication they needed to use if pain level was not reduced enough by the experimental treatment.

Following end of treatment, there were follow up interviews at 4, and 8 weeks post-treatment cessation, to see how long symptom attenuation, if any, persisted. These post-treatment evaluations were also used to discuss any side effects or adverse events that any of the study participants experienced. After the 8-week post treatment interview and data gathering, patients were dismissed from the study.

Study groups were compared using $X^2$ analysis and paired t-tests using SPSS, version 25. Adverse events were calculated by the quantitative method of Mastroianni et al. (Mastroinanni, 2017).

The study employed Resman Research Management (RRMS) software to manage the trial data. The participants in the trial were randomized by RRMS software. Participants that fulfilled the inclusion criteria were randomly allocated into one of the four treatment groups, with the desired end goal of equal distribution to all four groups. The RRMS software created unique identification codes for each participant. Prior to the study commencing, all involved researchers received training in allocation concealment. Randomization and allocation were managed and password-controlled in the RRMS software by a pre-designated member of the research team. This person was not involved in the direct screening or enrolling of participants. Screeners, and enrollers, and statisticians were blinded to the identification of each participant (Li 2017).

REFERENCES

Aley, K., et al., Nitric Oxide Signaling in Pain and Nociceptor Sensitization in the Rat, *Journal of Neuroscience* 1 Sep. 1998, 18 (17) 7008-7014.

Arzi, A., et al., Antinociceptive Effect of Hydroalcoholic Extract of Iranian Green tea in the Formalin Test in Rats, *Jundishapur journal of natural pharmaceutical products,* 8(1), 10-4 (2013).

Backes, M., *Cannabis* pharmacy: The practical guide to medical marijuana, New York: Black Dog & Leventhal (2017).

Baron, E. P., Comprehensive Review of Medicinal Marijuana, Cannabinoids, and Therapeutic Implications in Medicine and Headache: What a Long Strange Trip It's Been, *Headache,* 55(6), 885-916 (2015).

Bensky, D., Chinese herbal medicine: *Materia medica,* Seattle, Wash.: Eastland Press (2004).

Bimonte, S., et al., The roles of epigallocatechin-3-gallate in the treatment of neuropathic pain: an update on preclinical in vivo studies and future perspectives, *Drug design, development and therapy,* 11, 2737-2742 (2017).

Blunder, M., et al., Polyacetylenes from Radix et Rhizoma Notopterygii Incisi with an Inhibitory Effect on Nitric Oxide Production In Vitro, *Planta Medica*, 80(05), 415-418 (2014).

Brand, E. J., & Zhao, Z., *Cannabis* in Chinese Medicine: Are Some Traditional Indications Referenced in Ancient Literature Related to Cannabinoids? *Frontiers in Pharmacology*, 8, 108 (2017).

Cheng-Jian Zheng, et al., Antinociceptive activities of the liposoluble fraction from *Vitex negundo* seeds, *Pharmaceutical Biology*, 48:6, 651-658 (2010).

Chinese Pharmacopoeia Commission (CP) Pharmacopoeia of the People's Republic of China, 2015 Edn. Beijing: China Medical Science Press (2015).

Classification and diagnostic criteria for headache disorders, cranial neuralgias and facial pain, Headache Classification Committee of the International Headache Society, Cephalalgia 1988.

Deyo, R. and Musty, R., A Cannbichromene (CBC) Extract Alters Behavioral Despair on the Mouse Tail Suspension Test of Depression, Proceedings 2003 Symposium on the Cannabinoids, Cornwall, ON (2003).

Ding, Y. J., & He, X. X., Traditional Chinese herbs in treatment of neurological and neurosurgical disorders, *The Canadian Journal Of Neurological Sciences*, 13(3), 210-213 (1986).

Editorial Committee, Great Encyclopedia of Chinese Medicinals (Zhong Yao Da Ci Dian). Shanghai: Shanghai Technology Press, 2220-2225 (1977).

Espi-López, G., Efficacy of Manual and Manipulative Therapy in the Perception of Pain and Cervical Motion in Patients With Tension-Type Headache: A Randomized, Controlled Clinical Trial, *Journal of Chiropractic Medicine*, 13(1), 4-13 (2014).

Feliú, A., et al., A Sativex®-like combination of phytocannabinoids as a disease-modifying therapy in a viral model of multiple sclerosis, *British journal of pharmacology*, 172(14), 3579-95 (2015).

G. D. Solomon and K. L. Price, "Burden of migraine. A review of its socioeconomic impact," PharmacoEconomics, vol. 11, no. 1,pp. 1-10, 1997.

Hampson, A. J., et al., "Cannabidiol and Delta-9-Tetrahydrocannabinol are Neuroprotective Antioxidants," *Proceedings of the National Academy of Sciences of the United States* 95, no. 14 8268-73 (1998).

He, D. Y., & Dai, S. M., Anti-inflammatory and immunomodulatory effects of *Paeonia lactiflora* pall, a traditional Chinese herbal medicine, *Frontiers in pharmacology*, 2, 10 (2011).

Hu, S., et al., The Analgesic and Antineuroinflammatory Effect of Baicalein in Cancer-Induced Bone Pain, *Evidence-based complementary and alternative medicine: eCAM*, 2015, 973524 (2015).

Hurtado-Gonzalez, P., et al., Effects of Exposure to Acetaminophen and Ibuprofen on Fetal Germ Cell Development in Both Sexes in Rodent and Human Using Multiple Experimental Systems, Environmental Health Perspectives, 126(4), 047006 (2018).

International Headache Society, "ICH-10 guide for headaches," Cephalalgia, vol. 17, pp. 1-82, 1997.

Kroll, L. S., et al, Level of physical activity, well-being, stress and self-rated health in persons with migraine and co-existing tension-type headache and neck pain, The Journal Of Headache And Pain, 18(1), 46 (2017).

Li, R., et al., Antiaging and Anxiolytic Effects of Combinatory Formulas Based on Four Medicinal Herbs, *Evidence-Based Complementary & Alternative Medicine (ECAM)*, 2017, 1-15 (2017).

Li, X., et al., Acupuncture paired with herbal medicine for prediabetes: study protocol for a randomized controlled trial, *Trials*, 18(1), 297 (2017).

Liu, Z., et al., A traditional Chinese formula composed of Chuanxiong Rhizoma and Gastrodiae Rhizoma (Da Chuanxiong Formula) suppresses inflammatory response in LPS-induced RAW 264.7 cells through inhibition of NF-κB pathway, *Journal Of Ethnopharmacology*, 19620-28 (2017).

Lochte, B. C., et al., The Use of *Cannabis* for Headache Disorders, *Cannabis and cannabinoid research*, 2(1), 61-71 (2017).

Macdonald, T. M., et al., Methodology of a large prospective, randomised, open, blinded endpoint streamlined safety study of celecoxib versus traditional non-steroidal anti-inflammatory drugs in patients with osteoarthritis or rheumatoid arthritis: protocol of the standard care versus celecoxib outcome trial (SCOT), *BMJ open*, 3(1), e002295 (2013).

McKay, D. L. and Blumberg, J. B., A review of the bioactivity and potential health benefits of peppermint tea (*Mentha piperita* L.), Phytother. Res., 20: 619-633 (2006).

Maccarrone, M., et al., Endocannabinoid signaling at the periphery: 50 years after THC, *Trends in pharmacological sciences*, 36(5), 277-96 (2015).

Mastroianni P., et al., Development of an Instrument to Report and Assess Causality of Adverse Events Related to Herbal Medicines, Vitae, Revista De La Facultad De Ciencias FarmaCéuticas Y Alimentarias, Vol. 24(1), 13-22 (2017).

Millea, P., Brodie, J., "Tension Type Headache" American Family Physician., 66(5):797-805 (2002).

Mini, J., *Marijuana syndromes: How to balance and optimize the effects of Cannabis with traditional Chinese medicine*, North Charleston, S.C.: Createspace (2011).

Nardi, G. M., et al., Anti-inflammatory Activity of Berry Fruits in Mice Model of Inflammation is Based on Oxidative Stress Modulation, *Pharmacognosy research*, 8(Suppl 1), S42-9 (2016).

Pacher, P. Batkai, S. Kunos, G., "The endocannabinoid System as an Emerging Target of Pharmacotherapy," Pharmacological Review 58, no. 3, 389-462 (2006).

Philippe, D., et al., Anti-inflammatory effects of Lacto-Wolfberry in a mouse model of experimental colitis, *World journal of gastroenterology*, 18(38), 5351-9 (2012).

Plaisance, K. I., Toxicities of drugs used in the management of fever, Clinical Infectious Diseases: An Official Publication Of The Infectious Diseases Society Of America, 31 Suppl 5S219-S223 (2000).

Rapoport A, et al., Analgesic rebound headache in clinical practice: data from a physician survey, *Headache*, 36:14-9 (1996).

Ratnam, E. V., *Cannabis indica*, Journal British Medical Association, Ceylon Branch, 13; 30-34 (1916).

Riley, D., *Treating pain with traditional Chinese medicine*, Brookline, Mass.: Paradigm (2003).

Russo E, *Cannabis* for migraine treatment: the once and future prescription? An historical and scientific review, Pain 76:3-8 (1998).

Ryu, K. H., et al., Anti-Inflammatory and Analgesic Activities of SKLJI, a Highly Purified and Injectable Herbal Extract of *Lonicera japonica*, Bioscience, Biotechnology, and Biochemistry, Volume 74, Issue 10, Pages 2022-2028 (2010).

Russo E., "Taming THC: Potential *Cannabis* Synergy an Phytocannabinoid-Terpenoid Entourage Effects," *British Journal of Pharmacology* 163, no. 7 (2011):1344-64 (2011).

Shan, C.-S., et al., Chuanxiong Formulae for Migraine: A Systematic Review and Meta-Analysis of High-Quality Randomized Controlled Trials, *Frontiers in Pharmacology*, 9, 589 (2018).

Siff, S., The Illegalization of Marijuana: A Brief History-|Origins: Current Events in Historical Perspective, Retrieved from http://origins.osu.edu/article/illegalization-marijuana-brief-history (2014, May).

Sun, P., *The treatment of pain with Chinese herbs and acupuncture*, Edinburgh: Elsevier Churchill Livingstone (2011).

Sun, W., et al., Gastrodin inhibits allodynia and hyperalgesia in painful diabetic neuropathy rats by decreasing excitability of nociceptive primary sensory neurons, *PloS one*, 7(6), e39647 (2012).

Tao, H. J., (Originally Liang Dynasty), Japan-Mori Risshi, Complete Compendium of Chinese Materia Medica, Vol. 5, Collection of Commentaries on the Classic of Materia Medica. Beijing: Huaxia Publishing House (1999).

Tong, YanQing, et al., "Chinese Herbal Therapy for Chronic Tension-Type Headache." Evidence-Based Complementary & Alternative Medicine (Ecam) 2015, 1-4, Alt HealthWatch, EBSCOhost (accessed Jun. 26, 2018).

Wang, B., et al., Antioxidant and anti-inflammatory activities of aqueous extracts of *Schizonepeta tenuifolia* Briq, *Food and Chemical Toxicology*, 50(3-4), 526-531 (2012).

Wang, M., et al., Anti-inflammatory and cytotoxic effects of methanol, ethanol, and water extracts of *Angelicae Dahuricae Radix*. *Journal of Oral Science*, 58(1), 125-131 (2016).

World Health Organization., & Lifting the Burden (Organization), *Atlas of headache disorders and resources in the world* 2011, Geneva: World Health Organization (2011).

Wu, L. Q., et al., Antinociceptive Effects of Prim-O-Glucosylcimifugin in Inflammatory Nociception via Reducing Spinal COX-2, *Biomolecules & therapeutics*, 24(4), 418-25 (2016).

Xiao, M. M., et al., Gastrodin protects against chronic inflammatory pain by inhibiting spinal synaptic potentiation, *Scientific reports*, 6, 37251 (2016).

Yang, H.-Y., et al., Chinese Herbs Containing Aristolochic Acid Associated with Renal Failure and Urothelial Carcinoma: A Review from Epidemiologic Observations to Causal Inference, *BioMed Research International*, 2014, 569325 (2014).

Yang, L., et al, Spasmolytic Mechanism of Aqueous Licorice Extract on Oxytocin-Induced Uterine Contraction through Inhibiting the Phosphorylation of Heat Shock Protein 27, *Molecules* 22, 1392 (2017).

Zhang Y, et al, A novel analgesic isolated from a traditional Chinese medicine, Curr Biol 24(2):117-23 (2014).

Zhou, J., et al., Paeoniflorin and Albiflorin Attenuate Neuropathic Pain via MAPK Pathway in Chronic Constriction Injury Rats, *Evidence-based complementary and alternative medicine: eCAM*, 2016, U.S. Pat. No. 8,082,753 (2016).

What is claimed:

1. A method of treating a headache in a human in need thereof, comprising administering to the human a therapeutically effective amount of a composition comprising an emulsification of (a) *Cannabis* oil and (b) an aqueous ethanol extract mixture of *Corydalis yanhusuo, Scutellaria baicalensis, Ligusticum chuangxiong, Mentha Haplocalyx, Angelica dahurica, Notopterygium incisum, Schizonepeta tenuifolia, Saposhnikovia divaricate, Glycyrrhiza uralensis, Lonicera japonica, Juncus effuses, Vitex trifolia, Gastrodia elata, Lycium barbarum*, and *Paeonia lactiflora*, wherein the extracts are used at a ratio of 12:8:12:24:6:12:4.5:6:6:9:3:9:6:15:12.

2. The method of claim 1, wherein the composition comprises from about 1 mg to about 100 mg of cannabinoids per mg of aqueous ethanol extract mixture.

3. The method of claim 1, wherein the composition comprises about 0.01 mg to 0.1 mg of terpenes per mg of composition.

4. The method of claim 1, wherein the composition comprises a mass ratio of tetrahydrocannabinol:cannabidiol between 2:1 to 10:1.

5. The method of claim 1, wherein the composition is prepared by a method comprising:
extracting *Cannabis* with an oil to produce a *Cannabis* oil;
extracting the extracts with aqueous ethanol; and
emulsifying the *Cannabis* oil with the extracts of claim 1.

6. The method of claim 5, wherein the *Cannabis* is immersed in oil for about 6 hours to about 10 hours, and then the solids in the oil are removed to form the aqueous alcohol extract mixture.

7. The method of claim 5, wherein extracting the *Cannabis* with oil comprises immersing the *Cannabis* in oil, wherein about 3.3 mL to about 4.5 mL of oil is used per gram of *Cannabis*.

8. The method of claim 5, wherein extracting the extracts with aqueous ethanol comprises immersing the extracts in aqueous ethanol for about 12 to about 36 hours, and removing solids to form the extract mixture.

9. The method of claim 5, wherein extracting the extracts with aqueous ethanol comprises immersing the extracts in aqueous ethanol, wherein about 0.5 mL to about 2 mL of aqueous ethanol is used per gram of the extract mixture.

10. The method of claim 5, wherein the aqueous ethanol comprises from about 40 v/v % to about 60 v/v % ethanol.

11. The method of claim 5, wherein emulsifying comprises emulsifying from about 1 mL to about 100 mL of *Cannabis* oil with about 100 mL to about 200 mL of the extract mixture.

12. The method of claim 5, wherein the emulsifying comprises sonication.

* * * * *